United States Patent [19]
Rytky et al.

[11] Patent Number: 5,690,119
[45] Date of Patent: Nov. 25, 1997

[54] METHOD AND SYSTEM FOR MEASURING HEARTBEAT RATE USING TELEMETRIC DATA TRANSMISSION

[75] Inventors: Pekka Rytky, Oulu; Erkki Loponen, Ruukki; Tapani Lähdesmäki, Oulu, all of Finland

[73] Assignee: Polar Electro Oy, Kempele, Finland

[21] Appl. No.: 652,713

[22] Filed: May 30, 1996

[30] Foreign Application Priority Data

May 31, 1995 [FI] Finland ................................. 952657

[51] Int. Cl.$^6$ ................................................. A61N 5/04
[52] U.S. Cl. ................................. 128/706; 128/903
[58] Field of Search ................................. 128/697, 706, 128/707, 903

[56] References Cited

U.S. PATENT DOCUMENTS

| | | |
|---|---|---|
| 4,223,678 | 9/1980 | Langer et al. . |
| 4,571,589 | 2/1986 | Slocum et al. ........................ 607/32 |
| 5,081,987 | 1/1992 | Nigam . |
| 5,113,869 | 5/1992 | Nappholz et al. . |
| 5,157,604 | 10/1992 | Axford et al. ........................ 128/705 |
| 5,251,326 | 10/1993 | Silverman . |
| 5,342,408 | 8/1994 | de Coriolis et al. ................. 607/32 |

FOREIGN PATENT DOCUMENTS

| | | |
|---|---|---|
| 0 472 411 A1 | 2/1992 | European Pat. Off. . |
| 0556 823 A3 | 8/1993 | European Pat. Off. . |
| 0 627 194 A2 | 12/1994 | European Pat. Off. . |
| 2 259 772 | 3/1993 | United Kingdom . |
| WO 92/21106 | 11/1992 | WIPO . |
| WO 94/02904 | 2/1994 | WIPO . |
| WO 94/21171 | 9/1994 | WIPO . |

Primary Examiner—William E. Kamm
Attorney, Agent, or Firm—Hoffmann & Baron, LLP

[57] ABSTRACT

The invention relates to a method and system for measuring heartbeat rate using telemetric data transmission. In the method, a heartbeat rate signal is measured from the object to be measured by using a telemetric transmitter unit which detects the signals. The heartbeat data is transmitted by inductive coupling to a telemetric receiver unit, and stored in a memory means within the receiver unit, and transferred by inductive coupling from the receiver unit to a data transfer unit, and transferred from the data transfer unit to a data processing unit. According to the invention, telemetric data transfer is also carried out from the data transfer unit to the receiver unit, and that data transfer in this direction is carried out by supplying one or more setting parameters from the data processing unit prior to the actual heartbeat measurement. These parameters are transferred via the data transfer unit to the receiver unit by inductive coupling between the data transfer unit and the receiver unit.

30 Claims, 4 Drawing Sheets

METHOD AND SYSTEM FOR MEASURING HEARTBEAT RATE USING TELEMETRIC DATA TRANSMISSION

BACKGROUND OF THE INVENTION

1. Field of the Invention

The present invention relates to a method for measuring heartbeat rate using telemetric data transmission, the method comprising the steps of measuring a heartbeat rate signal from the object to be measured by using a telemetric transmitter unit which detects the signals and by means of which the heartbeat data is telemetrically transmitted by inductive coupling to a telemetric receiver unit, storing the heartbeat data in a memory means within the receiver unit, transferring the heartbeat data by inductive coupling from the receiver unit to a data transfer unit, and transferring the heartbeat data from the data transfer unit to a data processing unit.

The invention further relates to a system for measuring heartbeat rate using telemetric data transmission, the system comprising a telemetric transmitter unit which comprises means for detecting and transmitting the heartbeat rate signals, a telemetric receiver unit for receiving the heartbeat rate signals from the telemetric transmitter unit by inductive coupling and for counting the heartbeat rate signals, a data transfer unit to which the receiver unit is connected by telemetric inductive coupling, and a data processing unit which is in communication with the data transfer unit.

The invention further relates to a method which utilizes telemetric data transmission for measuring the heartbeat rate, and which uses a telemetric transmitter unit for measuring the heartbeat rate from the object to be measured.

The term transmitter unit particularly refers to a unit provided with electrodes that is kept against a human body, and which is often realized in the shape of a transmitter belt. The term receiver unit refers, for example, to a receiver unit which is worn on a wrist and which is telemetrically connected to the transmitter unit.

The heartbeat measurement is based on monitoring the functioning of the heart. As the heart contracts, it provides a series of electric pulses that can be measured on the body. Measuring and analyzing this signal is referred to as electrocardiography (ECG). The signal itself is referred to as an ECG signal. From the ECG signal, the various phases of the cardiac cycle can be identified. These parts are the so-called P, Q, R, S, T and U waves.

2. Description of the Prior Art

In the prior art methods and systems inductive data transmission takes place in one direction only, i.e. at the measuring phase when heartbeat data is being transferred from the transmitter unit to the receiver unit, and at the data recall, i.e. unloading, phase as the heartbeat data is being transferred from the receiver unit to the data transfer unit, i.e. the reading device. Due to the unidirectional data transmission, the use of the methods and systems may at times be difficult, if for example a trainer has no knowledge or experience of using the systems. Furthermore, the prior art systems employing inductive transfer all require the use of both a transmitter unit and a receiver unit. The drawbacks of the prior art become especially obvious when the measurement contents of several heartbeat rate monitors should be read.

SUMMARY OF THE INVENTION

It is an object of the present invention to provide a new type of a method and system by means of which the prior art problems can be avoided.

In order to achieve this object, the invention is characterized by that which is set forth in the attached claims.

The invention provides several advantages. The method and system of the invention are easy to use and more versatile than before. The invention allows easy and wireless user-specific programming of the transmitter and receiver units, and a simple data transfer. A second embodiment of the invention additionally provides the noteworthy advantage that the use of a receiver unit is not required, which means that the advantages of the invention still become more evident and a cost-efficient solution is obtained. The control procedures concerning heartbeat data transfer are carried out solely by means of the data processing unit; accordingly, the user need not be familiar with difficult keyboard features of the receiver or transmitter unit that the prior art solution use to control data transfer with.

BRIEF DESCRIPTION OF THE DRAWINGS

In the following the invention will be described in greater detail with reference to the attached drawings, in which.

DESCRIPTION OF THE PREFERRED EMBODIMENTS

Figure 1:
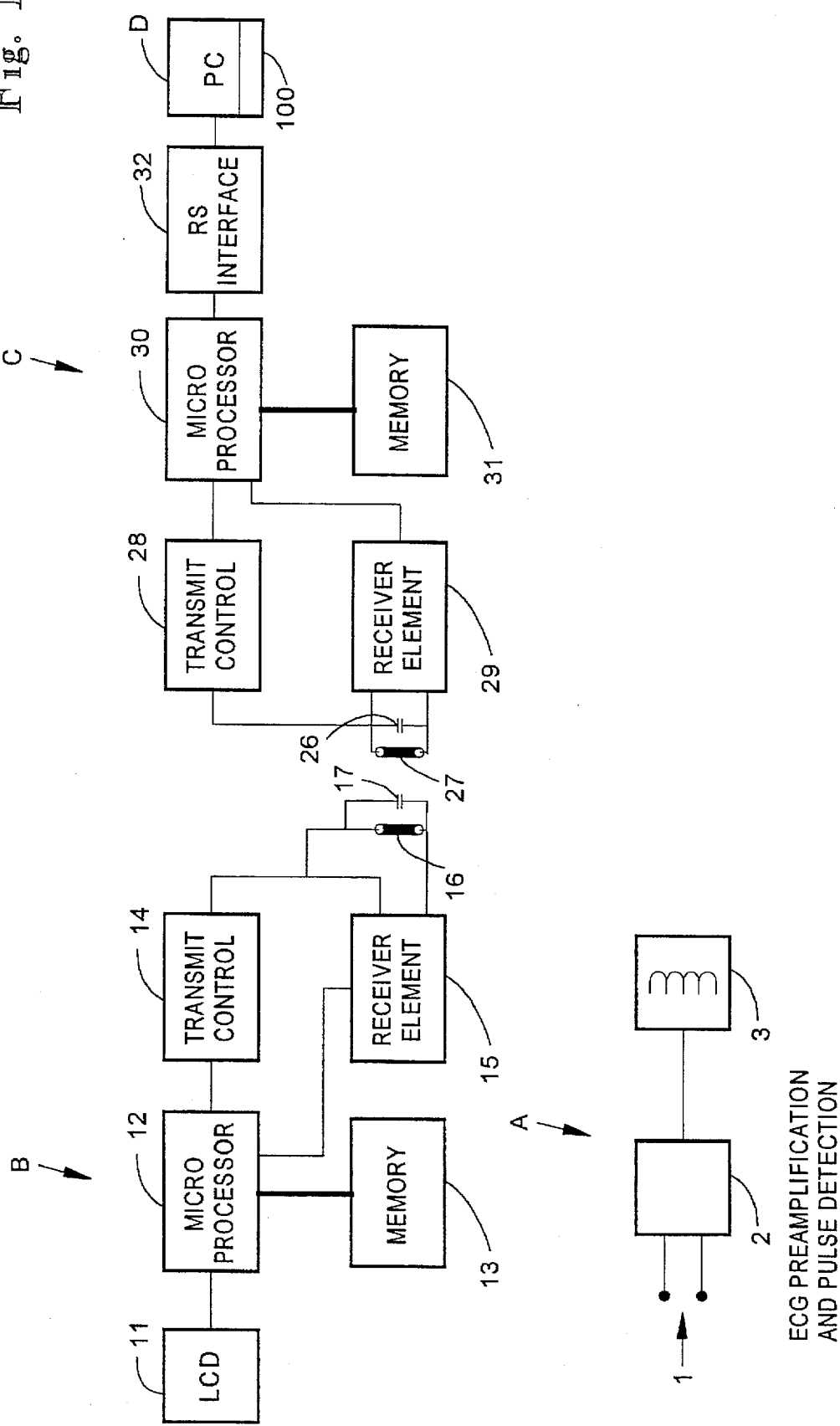
FIG. 1 illustrates a system in accordance with the first embodiment of the invention.

FIG. 1 illustrates a system employing telemetric data transmission for measuring the heartbeat rate. The principal components of the system are a telemetric transmitter unit A, a telemetric receiver unit B, a data transfer unit C, and a data processing and control unit D such as a personal computer. In the first embodiment according to FIG. 1 a transmitter unit A known per se can be used that comprises ECG electrodes 1, ECG preamplification and pulse detection block 2, and inductance 3. Block 2 provides as an output a heartbeat rate signal controlling the inductance 3, the time interval between the pulses being equal to the heartbeats. Thus, a magnetic field varying according to the heartbeats is generated in the inductance 3.

The telemetric receiver unit B comprises means 11-17: a display unit 11, a counter unit 12, such as a microprocessor 12, a memory 13, a transmitter controller 14, a receiver element 15, inductance 16 and capacitance 17. The display unit 11, such as an LCD display, provides the user with visual information, the microprocessor 12 controls logic functions, the memory 13 stores the heartbeat data, time information and other user-specific parameter information P of the performance, the transmitter controller 14 generates the data transfer from the receiver unit B to the data transfer unit C by utilizing inductance 16, the receiver element 15 receives by means of inductance 16 information as induced voltage from inductance 27 of the data transfer unit C and converts it into digital form, i.e. the form understood by the microprocessor 12. Inductance 16, such as a coil 16, is in parallel resonance with a capacitor 17 on the data transfer frequency being used.

The data transfer unit C comprises capacitance 26, inductance 27, a transmitter controller 28, a receiver element 29, a counter element, such as a microprocessor 30, a memory 31, and an RS232 interface 32. Via the interface 32, the data transfer unit C communicates with the data processing unit D, such as a personal computer D. Inductance 27 of the data transfer unit C is on the same resonance frequency as inductance 16 of the receiver unit. The purpose of the transmitter controller 28 is to generate a control signal for inductance 27. The purpose of the receiver element 29 is to receive the serial mode data from inductance 16, i.e. coil 16, by inductance 27. The microprocessor 30 converts the data transmission into a form suitable for a PC (data processing unit D). The memory 31 of the data transfer unit C can, when required, store files that have been read. The RS232 interface 32 transforms the voltage levels of the interface to be in accordance with the RS232 standard.

In the first embodiment of the invention, the system comprises a telemetric transmitter unit A which comprises means 1–3 for detecting and transmitting the heartbeat rate signals. In addition, the system comprises a telemetric receiver unit B, 11–17 for receiving the heartbeat rate signals from the telemetric transmitter unit A by inductive coupling 3, 16. At the counter unit 12 of the receiver unit B the heartbeat rate signals are counted, and the result can be written out on the display 11 and stored in the memory 13. The system also comprises a data transfer unit C to which the receiver unit B is connected by telemetric inductive coupling 16, 27. In addition, the system comprises a data processing unit D which communicates with the data transfer unit.

In the first embodiment of the invention, the system comprises means for transferring one or more setting parameters P, supplied by the data processing unit D, to the receiver unit B via the data transfer unit C by inductive coupling 27, 16 between the data transfer unit C and the receiver unit B. The means for transferring setting parameters P to the receiver unit B comprise a transmitter controller 28 contained in the data transfer unit C, said transmitter controller being connected to control the two-way inductive coupling between the data transfer unit C and the receiver unit B as concerns the inductive coupling associated with the data transfer unit C. Thus, the transmitter controller controls inductance 27. The device D comprises a supply means 100 used for supplying the parameters P. By means of the supply means, different kinds of control commands are additionally given.

The first embodiment of the invention is advantageously such that the two-way inductive coupling 16, 27 between the receiver unit B and the data transfer unit C comprises, in the receiver unit B, inductance 16 which is used both for receiving one or more setting parameters P from the data transfer unit C to the receiver unit B and for receiving heartbeat data from the transmitter unit A, and for transmitting the heartbeat data to the data transfer unit C. Consequently, inductance 16 has three different tasks simplifying the operation of the system and lowering its costs. In an advantageous embodiment according to the first embodiment of the invention, the two-way inductive coupling 16, 27 between the receiver unit B and the data transfer unit C comprises, in the data transfer unit C, inductance 27 which is employed both for transmitting one or more setting parameters P from the data transfer unit C to the receiver unit B and for receiving heartbeat data from the receiver unit B. Thus, inductance 27 has two different purposes, simplifying the operation of the system and lowering costs.

As to the method, the first embodiment relates to a method for measuring the heartbeat rate by using telemetric data transmission, in which method the heartbeat rate signal is measured from the object to be measured by utilizing a telemetric transmitter unit A which detects the heartbeat rate signals, the transmitter unit A being used for transmitting the heartbeat data to the telemetric receiver unit B by inductive coupling 3, 16. In addition, the heartbeat data is stored in the system to a memory means 13 within the receiver unit B. Furthermore, the heartbeat data is transferred in the method from the receiver unit B to the data transfer unit C by inductive coupling 16, 27, and the heartbeat data is transferred from the data transfer unit C to the data processing unit D. As regards the aforementioned, the method is known per se. In addition to the heartbeat data, internal settings are transferred from the receiver unit B to the personal computer D via the data transfer unit C.

According to the actual invention, the method in its first embodiment contains carrying out telemetric data transfer from the data transfer unit C to the receiver unit B, and that data transfer in this direction is carried out by supplying one or more setting parameters P from the data processing unit D prior to the actual heartbeat measurement. These parameters P are transferred via the data transfer unit C to the receiver unit B by inductive coupling 27, 16 between the data transfer unit C and the receiver unit B.

The preferred first embodiment of the method according to the invention is such that the telemetric data transmission in said direction from the data transfer unit C to the receiver unit B is in addition carried out by giving control commands CC to the receiver unit B concerning data transmission, the control commands controlling telemetric data transfer of heartbeat data from the receiver unit B to the data transfer unit C.

The preferred first embodiment of the method according to the invention is such that the method utilizes in the reception of one or more setting parameters P from the data transfer unit C, in the receiver unit B, the same inductance means 16 as is used for receiving heartbeat data from the transmitter unit A (its inductance 3) and transferring the heartbeat data from the receiver unit B to the data transfer unit C. In this preferred embodiment of the method, the same inductance means 27 is utilized in the data transfer unit C for transferring one or more setting parameters P from the data transfer unit C to the receiver unit B as is used in the reception of heartbeat data from the receiver unit B (its inductance 16). This results in that the method functions in a simple and, as far as the inductances are concerned, a versatile manner.

The preferred first embodiment of the method according to the invention is such that the method comprises in the receiver unit B a field strength selector on whether the received signal is a low level signal from the transmitter unit A, or a considerably higher level signal transmitted by the data transfer unit C. In this manner, it is possible to adjust measurement sensitivity. This is carried out by the message (FIG. 5) transmitted by the data transfer unit C having as a setting parameter one parameter on the basis of which the receiver unit B selects the measurement sensitivity. In other words, the receiver unit B comprises means for selecting measurement sensitivity on the basis of the parameter received from the data transfer unit C.

The preferred first embodiment of the method according to the invention is such that prior to the actual heartbeat rate measurement at least a user identification information ID is fed from the data processing unit D, PC to the receiver unit B as the setting parameter P, and that following the heartbeat rate measurement upon transferring the heartbeat data telemetrically from the receiver unit B to the data transfer unit C by inductive coupling 16, 27 the heartbeat data is transferred telemetrically so that the heartbeat data is incorporated with the user identification information ID. This makes it possible to obtain without any difficult keyboard operations carried out by the user such a reading operation that is able to associate each user with his heartbeat data. This is particularly important in team games.

The preferred first embodiment of the method according to the invention is such that prior to the actual heartbeat rate measurement two or more of the following setting parameters are fed from the data processing unit D to the receiver unit B as the setting parameters P; user identification information ID, clock settings, calendar settings, threshold levels for heartbeat rate measurements, alarm limits for the heartbeat rate measurements, settings for alarm timers, measurement settings for recovery, measurement sensitivity adjustment, selection of information on the display, and text information. In this manner, all the control procedures can be carried out from the personal computer, i.e. the data processing and control unit D. Such a practice considerably facilitates using the system.

The preferred first embodiment of the method according to the invention is such that the transfer of one or more setting parameters from the data processing unit D to the receiver unit B via the data transfer unit C is activated by bringing the receiver unit B and the data transfer unit C close to each other, and giving a transfer command from the data processing unit D. In this manner, the setting parameters can be transferred without difficulties. Furthermore, the preferred first embodiment of the invention is such that the telemetric transfer of heartbeat data from the receiver unit B to the data transfer unit C is activated simply by bringing the receiver unit B and the data transfer unit C close to each other, and if necessary by giving the command to start from the data processing unit D.

The preferred method is such that when the data processing unit C is functionally uncoupled to the data processing unit D, the transfer of heartbeat data simply begins by bringing the receiver unit B and the data transfer unit C close to each other. In such a case, the data transfer unit C indicates its read state with an indicator 50, such as a LED component.

The embodiments described in the above simplify and facilitate using the method and the system.

Figure 2:
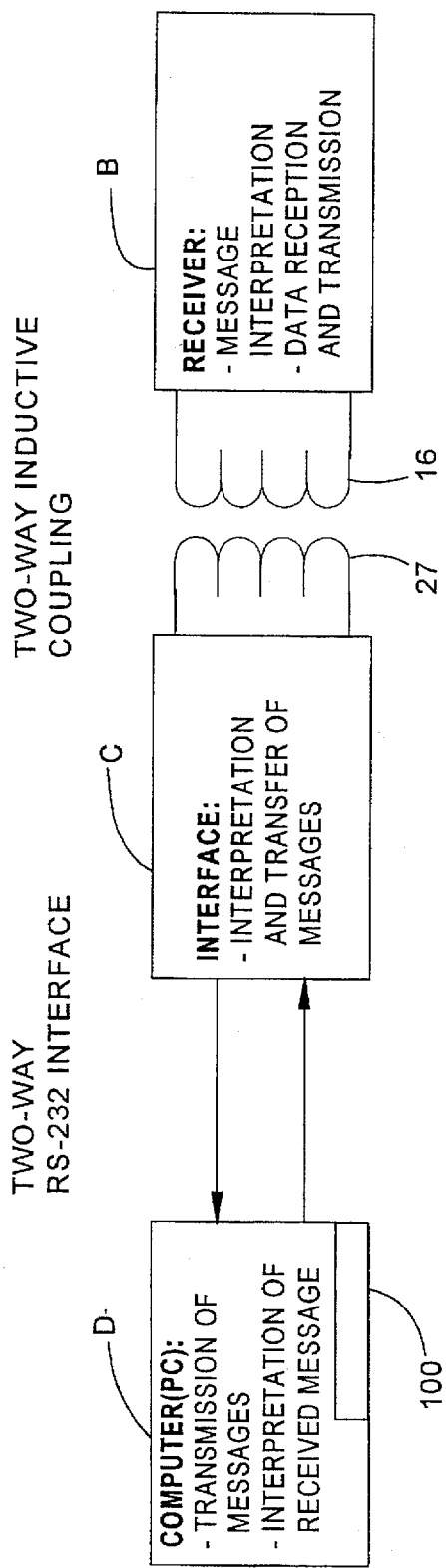
FIG. 2 is a simplified block diagram of the system according to the first embodiment of the invention.
Figure 5:
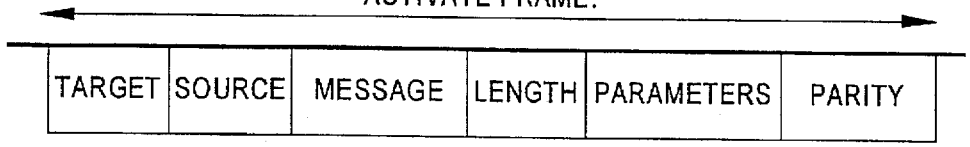
FIG. 5 shows, associated with the first embodiment, an activation message transmitted by the data processing unit.
Figure 6:
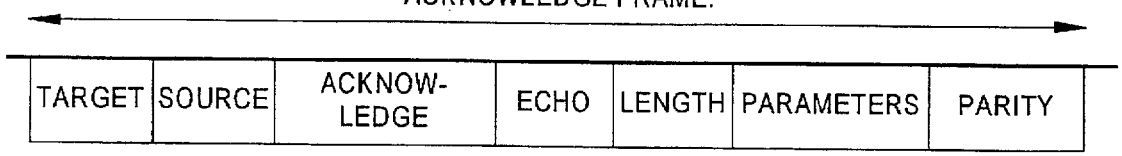
FIG. 6 shows, associated with the first embodiment, an acknowledgement message transmitted by either the receiver unit or the data transfer unit.

FIGS. 5–6 illustrate, in association with FIG. 2 in particular, messages that the system conveys. The messages are divided in two categories. The personal computer D transmits "Activate Frame" messages, such as in FIG. 5. A peripheral device, such as the data transfer unit C or the receiver unit B responds with an "Acknowledge Frame" message. The data processing and control unit D functions as a so-called master device, and it is able to command the peripheral device B or C to any state it desires, even during another function.

Figure 3:
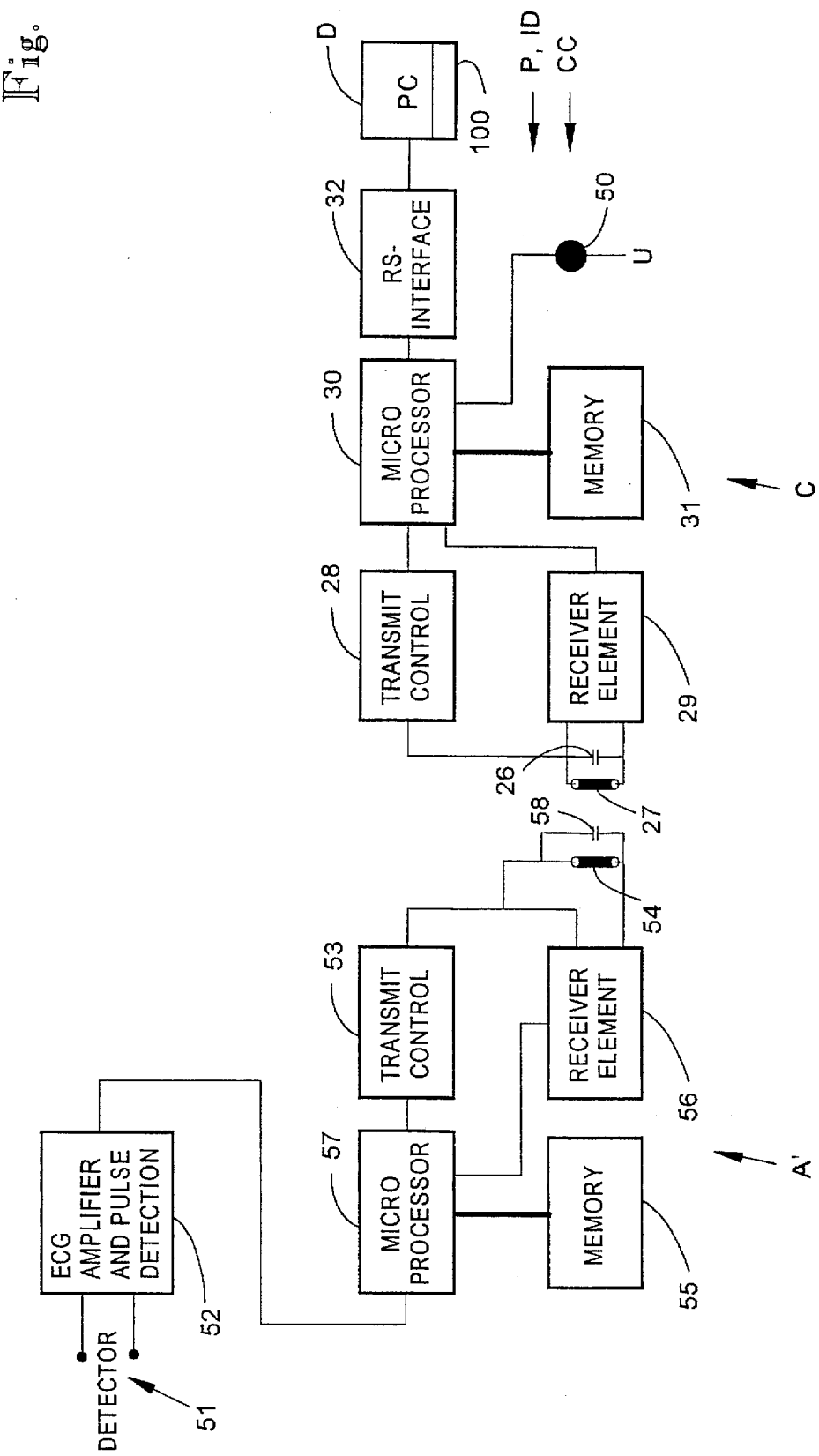
FIG. 3 illustrates a system in accordance with the second embodiment of the invention.
Figure 4:
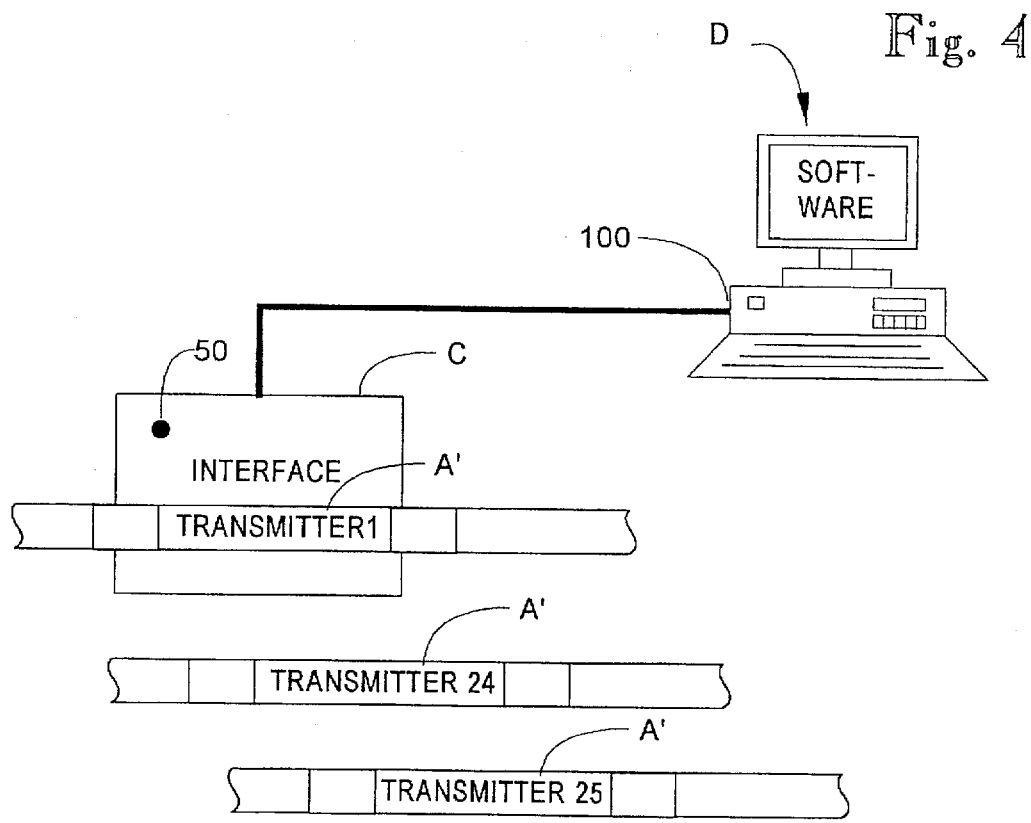
FIG. 4 is a simplified block diagram of the system according to the second embodiment of the invention.

FIGS. 3–4 are related to a second preferred embodiment of the invention: in this embodiment the use of a telemetric receiver unit, i.e. the so-called heart monitor, worn on a wrist is not necessarily required.

FIGS. 3–4 relate to a telemetric system for heartbeat rate measurement. The system comprises a telemetric transmitter unit A'. The essential feature of the second embodiment relates in particular to the structure and operation of the transmitter unit A'. The system comprises, as in the first embodiment, a data transfer unit C, 26–32, which is described in closer detail in the above. In FIGS. 3–4, the transmitter unit comprises ECG electrodes 51, ECG preamplification and pulse detection block 52, a transmitter controller 53, as well as inductance 54 and capacitance 58, which are normal components of a transmitter unit. The essential features that differ from the prior art in the second embodiment of the invention are a memory 55, a receiver element 56 and a counter unit 57 such as a microprocessor within the transmitter unit A'. In FIG. 3, the block 53 supplies as an output a heartbeat rate signal that controls inductance 54, the signal having a pulse interval matching that of the heartbeats. Thus, a magnetic field varying according to the heartbeat rate is generated in inductance 54.

Referring to FIGS. 3–4, the second embodiment of the invention also relates to a method for measuring a person's heartbeat rate by using telemetric data transmission. In the normal manner, the heartbeat rate is measured from the object to be measured by means of a telemetric transmitter unit A', 51–57 which detects the heartbeat signals. According to the second embodiment of the method, it is inventive that the method for measuring the heartbeat rate utilizes such a telemetric transmitter unit A' which comprises a counter unit 57, a memory means 55 and a receiver 56. According to the invention, in the second embodiment of the method the heartbeat data processed in the counter unit 57 is stored in the memory means 55 within the transmitter unit A'. The heartbeat data is transferred by inductive coupling 54, 27 from the memory of the transmitter unit A' to the data transfer unit C from which it is transferred to the data processing unit D. In the method, telemetric data transmission is also carried out from the data transfer unit C to the transmitter unit A', and data transmission in said direction is carried out so that prior to the actual heartbeat rate measurement the data processing unit D supplies one or more setting parameters which, via the data transfer unit C, are transferred to the memory 55 of the transmitter unit A' by inductive coupling 24, 54 between the data transfer unit C and the receiver element within the transmitter unit A'. In contrast to prior art solutions, the second embodiment of the invention provides a telemetric transmitter unit A' equipped with a memory 55 which can be read inductively. With this telemetric transmitter unit A', it is not necessary to use a telemetric receiver unit in contrast to the prior art solutions and the first embodiment (receiver unit B) of the invention. If desired, a simple receiver unit can be used, i.e. a heartbeat rate monitor on a person's wrist, by means of which warnings on heartbeat rate can be given.

In the second embodiment of the invention, the method is preferably such that telemetric data transmission in said direction from the data transfer unit C to the transmitter unit A' is in addition carried out by giving control commands CC concerning data transfer to the transmitter unit A', said commands controlling telemetric data transfer of heartbeat data from the transmitter unit A' to the data transfer unit C.

In the second embodiment of the invention, the method is preferably such that the receiver unit A' uses, in the reception of one or more setting parameters P from the data transfer unit D, the same inductance means 54 as used for transmitting the heartbeat data from the transmitter unit A' to the data transfer unit C. Furthermore, in the preferred embodiment, the method utilizes in the data transfer unit C the same inductance means 27 for transmitting one or more setting parameters to the memory 55 of the transmitter unit A' as used for receiving the heartbeat data from the transmitter unit A'.

In the second embodiment of the invention, the method is preferably such that prior to the actual heartbeat rate measurement at least a user identification information ID is supplied from the data processing unit D to the memory 55 within the transmitter unit A' as the setting parameter P, and that following the heartbeat rate measurement upon transferring the heartbeat data telemetrically from the transmitter unit A' to the data transfer unit C the heartbeat data is transferred telemetrically so that the heartbeat data is incorporated with the user identification information ID. As a result, the sportsperson or the trainer handling the system need not input any specific identifications as the system itself is capable of associating each user's heartbeat data with the correct user. Each user, i.e. each sportsperson in practice, uses a dedicated user identification, such as his game number.

In the second embodiment of the invention, the method is preferably such that the transfer of one or more setting parameters P from the data processing unit D to the memory 55 within the transmitter unit A' via the data processing unit C is activated by bringing the transmitter unit A' and the data transfer unit C close to each other, and giving the transfer command from the data processing unit D, i.e. the personal computer. In the preferred embodiment, the telemetric transfer of heartbeat data from the transmitter unit A' to the data transfer unit C is simply activated by bringing the transmitter unit A' and the data transfer unit C close to each other, and if necessary by giving the start command from the data processing unit C. The preferred embodiment is such that when the data transfer unit C is uncoupled to the data processing unit D, the transfer of heartbeat data to the data transfer unit C simply begins by bringing the transmitter unit A' and the data transfer unit C close to each other. In the preferred embodiment in such a case, the data transfer unit C indicates its read state with the indicator 50. The embodiments described above simplify the method and the usability of the system particularly in team games, or if a large number of users have to measured.

Although the invention is described above with reference to the examples in the attached drawings, it is obvious that the invention is not restricted thereto but it may be varied in many ways within the inventive idea of the attached claims.

What is claimed is:

1. A method for measuring heartbeat rate using two-way inductive data transmission, said method comprising the steps of:

(a) measuring a heartbeat rate signal from an object to be measured by using a means for detecting, storing and transmitting said heartbeat rate signal;

(b) storing heartbeat data, corresponding to said heartbeat rate signal, within said means for detecting, storing and transmitting said heartbeat rate signal;

(c) transferring said heartbeat data by inductive coupling from said means for detecting, storing and transferring said heartbeat rate signal to a data transfer unit;

(d) transferring said heartbeat data from said data transfer unit to a data processing unit; and (e) prior to step (a), transferring data comprising at least one setting parameter from said data processing unit to said means for detecting, storing and transmitting said heartbeat rate signal, through said data transfer unit, by inductive coupling between said data transfer unit and said means for detecting, storing and transmitting said heartbeat rate signal.

2. The method of claim 1, wherein said means for detecting, storing and transmitting said heartbeat rate signal includes a receiver unit, a transmitter unit which detects the signals and by means of which the heartbeat data is transmitted by inductive coupling to said receiver unit, and a memory means within said receiver unit, and wherein:

step (b) includes storing the heartbeat data in said memory means;

step (c) includes transferring the heartbeat data by inductive coupling from the receiver unit to said data transfer unit; and in step (e), said transferring is carried out through the data transfer unit to the receiver unit by inductive coupling between the data transfer unit and the receiver unit;

further comprising the additional step of:

(f) transmitting said heartbeat rate signal from said transmitter unit to said receiver unit by inductive coupling.

3. The method as claimed in claim 2, wherein step (e) includes the sub-step of giving control commands to the receiver unit concerning data transmission, the control commands controlling data transfer of said heartbeat data from the receiver unit to the data transfer unit.

4. The method as claimed in claim 2, wherein said means for detecting, storing and transmitting said heartbeat rate signal includes first inductance means and said data transfer unit includes second inductance means, wherein:

step (e) includes transmitting said at least one setting parameter from said second inductance means to said first inductance means;

step (f) includes receiving said heartbeat rate signal with said first inductance means; and step (c) includes transmitting said heartbeat data with said first inductance means and receiving said heartbeat data with said second inductance means.

5. The method as claimed in claim 2, further comprising the additional step of carrying out a field strength selection in the receiver unit on the basis of a received setting parameter concerning whether the received signal is a low level signal from the transmitter unit, or a considerably higher level signal transmitted by the data transfer unit.

6. The method as claimed in claim 2, wherein step (e) includes feeding, at least a user identification information from the data processing unit to the receiver unit as the at least one setting parameter, and step (c) includes transferring the heartbeat data so that the heartbeat data is incorporated with the user identification information.

7. The method as claimed in claim 2, wherein step (e) includes transferring at least two of the following setting parameters from the data processing unit to the receiver unit as the setting parameters: user identification information, clock settings, calendar settings, threshold levels for heartbeat rate measurements, alarm limits for the heartbeat rate measurements, settings for alarm timers, measurement settings for recovery, measurement sensitivity adjustment, selection of information on a display, and text information.

8. The method as claimed in claim 2, further comprising the additional steps of:

bringing the receiver unit and the data transfer unit close to each other to initiate step (e); and giving a transfer command from the data processing unit.

9. The method as claimed in claim 2, further comprising the additional step of bringing the receiver unit and the data transfer unit close to each other to initiate step (c).

10. The method as claimed in claim 9, further comprising giving a command to start from the data processing unit.

11. The method as claimed in claim 2, wherein the data transfer unit is uncoupled to the data processing unit, further comprising the additional steps of:

bringing the receiver unit and the data transfer unit close to each other; and indicating a read state of the data transfer unit with an indicator.

12. The method of claim 1, wherein said means for detecting, storing and transmitting said heartbeat rate signal includes a transmitter unit which comprises a counter unit, a memory means and a receiver;

further comprising the additional step of processing said heartbeat data in said counter unit; wherein:

step (b) includes storing the heartbeat data processed in the counter unit in the memory means within the transmitter unit;

step (c) includes transferring the heartbeat data by inductive coupling from the memory of the transmitter unit to the data transfer unit from which it is transferred to the data processing unit; and step (e) includes transferring said at least one setting parameter, via the data transfer unit, to the memory of the transmitter unit by inductive coupling between the data transfer unit and the receiver element within the transmitter unit.

13. The method as claimed in claim 12, wherein the receiver of the transmitter unit includes first inductance means, and wherein:

step (e) includes receiving said at least one setting parameter with said first inductance means; and step (c) includes transferring said heartbeat data with said first inductance means.

14. The method as claimed in claim 12, wherein step (e) includes supplying at least a user identification information from the data processing unit to the memory within the transmitter unit as the at least one setting parameter, and step (c) includes transferring the heartbeat data so that the heartbeat data is incorporated with the user identification information.

15. The method as claimed in claim 12, further comprising the additional steps of:

bringing the transmitter unit and the data transfer unit close to each other to initiate step (e); and giving a transfer command from the data processing unit.

16. The method as claimed in claim 12, further comprising the additional step of bringing the transmitter unit and the data transfer unit close to each other to initiate step (c).

17. The method as claimed in claim 16, further comprising giving a command to start from the data processing unit.

18. The method as claimed in claim 12, wherein the data transfer unit is uncoupled to the data processing unit, further comprising the additional steps of:

bringing the transmitter unit and the data transfer unit close to each other; and indicating a read state of the data transfer unit with an indicator.

19. The method as claimed in claim 12, wherein step (e) includes the sub-step of giving control commands concerning data transfer to the transmitter unit, said commands controlling data transfer of heartbeat data from the transmitter unit to the data transfer unit.

20. The method as claimed in claims 12 or 19, wherein the data transfer unit includes second inductance means, and wherein:

step (e) includes transmitting said at least one setting parameter with said second inductance means; and step (c) includes receiving said heartbeat data with said second inductance means.

21. A system for measuring heartbeat rate using two-way inductive data transmission, said system comprising:

means for detecting, storing and transmitting a heartbeat rate signal;

a data transfer unit connected to said means for detecting, storing and transmitting said heartbeat rate signal by two-way inductive coupling;

a data processing unit in communication with said data transfer unit; and means for transferring at least one setting parameter from said data processing unit to said means for detecting, storing and transmitting said heartbeat rate signal, through said data transfer unit, by said inductive coupling between said data transfer unit and said means for detecting, storing and transmitting said heartbeat rate signal.

22. The system of claim 21, wherein said means for detecting, storing and transmitting said heartbeat rate signal is a transmitter unit comprising:

pulse detection means for detecting a pulse and producing a heartbeat rate signal therefrom;

a counter unit which processes heartbeat data from said heartbeat rate signal;

a memory means which stores data processed by said counter unit; and a receiver which receives said at least one setting parameter from said data processing unit and transfers said at least one setting parameter to said memory means.

23. The system as claimed in claim 22, wherein the means for transferring the at least one setting parameter to the receiver of the transmitter unit comprises a transmitter controller contained in the data transfer unit, said transmitter controller being connected to control the two-way inductive coupling between the data transfer unit and the receiver of the transmitter unit as concerns the inductive coupling associated with the data transfer unit.

24. The system as claimed in claim 23, further comprising an inductance in the receiver of the transmitter unit, which is used both for receiving said at least one setting parameter from the data transfer unit and for transmitting the heartbeat data to the data transfer unit.

25. The system as claimed in claim 24, further comprising an inductance in the data transfer unit, which is employed both for transmitting said at least one setting parameter from the data transfer unit to the receiver of the transmitter unit and for receiving said heartbeat data from the transmitter unit.

26. The system as claimed in claim 23, further comprising an inductance in the data transfer unit, which is employed both for transmitting said at least one setting parameter from the data transfer unit to the receiver of the transmitter unit and for receiving said heartbeat data from the transmitter unit.

27. The system of claim 21, wherein said means for detecting, storing and transmitting said heartbeat rate signal includes:

a transmitter unit which comprises means for detecting and transmitting the heartbeat rate signals; and a receiver unit for receiving the heartbeat rate signals from the transmitter unit by inductive coupling, and for counting the heartbeat rate signals; and wherein:

said data transfer unit is connected to said receiver unit by said two-way inductive coupling; and the means for transferring at least one setting parameter transfers said at least one setting parameter to the receiver unit via the data transfer unit by inductive coupling between the data transfer unit and the receiver unit.

28. The system as claimed in claim 7, wherein the means for transferring the at least one setting parameter to the receiver unit comprises a transmitter controller contained in the data transfer unit, said transmitter controller being connected to control the two-way inductive coupling between the data transfer unit and the receiver unit as concerns the inductive coupling associated with the data transfer unit.

29. The system as claimed in claim 28, further comprising an inductance in the receiver unit, which is used for receiving said at least one setting parameter from the data transfer unit for receiving said heartbeat data from the transmitter unit, and for transmitting the heartbeat data to the data transfer unit.

30. The system as claimed in claims 28 or 29, further comprising an inductance in the data transfer unit, which is employed both for transmitting said at least one setting parameter from the data transfer unit to the receiver unit and for receiving said heartbeat data from the receiver unit.

* * * * *

UNITED STATES PATENT AND TRADEMARK OFFICE
CERTIFICATE OF CORRECTION

PATENT NO. : 5,690,119
DATED : November 25, 1997
INVENTOR(S) : Rytky, et al.

It is certified that error appears in the above-identified patent and that said Letters Patent is hereby corrected as shown below:

<u>In Column 10, Line 63,</u> the patent now reads "28. The system as claimed in claim 7"; this should read --28.

Signed and Sealed this

Twenty-fourth Day of March, 1998

Attest:

BRUCE LEHMAN

Attesting Officer

Commissioner of Patents and Trademarks